(12) United States Patent
Hu

(10) Patent No.: US 7,834,520 B2
(45) Date of Patent: Nov. 16, 2010

(54) ULTRASONIC PROBE AND ULTRASONIC DIAGNOSIS APPARATUS

(75) Inventor: Zhiqiang Hu, Chiba (JP)

(73) Assignee: Hitachi Medical Coporation, Tokyo (JP)

( * ) Notice: Subject to any disclaimer, the term of this patent is extended or adjusted under 35 U.S.C. 154(b) by 754 days.

(21) Appl. No.: 11/721,049

(22) PCT Filed: Dec. 8, 2005

(86) PCT No.: PCT/JP2005/022564

§ 371 (c)(1),
(2), (4) Date: Jun. 7, 2007

(87) PCT Pub. No.: WO2006/062164

PCT Pub. Date: Jun. 15, 2006

(65) Prior Publication Data

US 2008/0139945 A1    Jun. 12, 2008

(30) Foreign Application Priority Data

Dec. 9, 2004    (JP) .............................. 2004-356971

(51) Int. Cl.
*H04R 17/00* (2006.01)
(52) U.S. Cl. .................. 310/334; 600/437; 600/459
(58) Field of Classification Search .................. 310/334; 600/437, 459
See application file for complete search history.

(56) References Cited

U.S. PATENT DOCUMENTS

| | | | | |
|---|---|---|---|---|
| 5,156,050 A * | 10/1992 | Schmid et al. | .................. | 73/628 |
| 5,555,887 A * | 9/1996 | Fraser et al. | .................. | 600/472 |
| 5,648,942 A | 7/1997 | Kunkel, III | | |
| 5,738,100 A * | 4/1998 | Yagami et al. | .............. | 600/466 |
| 6,051,913 A | 4/2000 | King | | |
| 6,467,138 B1 | 10/2002 | Aime | | |
| 2002/0188200 A1* | 12/2002 | Mauchamp et al. | ......... | 600/439 |
| 2003/0029010 A1* | 2/2003 | Aime | ........................ | 29/25.35 |
| 2006/0186765 A1* | 8/2006 | Hashimoto | .................. | 310/334 |
| 2007/0276248 A1* | 11/2007 | Saito et al. | .................. | 600/459 |

FOREIGN PATENT DOCUMENTS

| | | |
|---|---|---|
| CN | 1550217 A | 12/2004 |
| EP | 0 727 259 A2 | 8/1996 |

(Continued)

OTHER PUBLICATIONS

Supplementary European Search Report, dated Mar. 18, 2010, issued in corresponding European Patent Application No. 05 81 4385.

*Primary Examiner*—Walter Benson
*Assistant Examiner*—Bryan P Gordon
(74) *Attorney, Agent, or Firm*—Antonelli, Terry, Stout & Kraus, LLP.

(57) ABSTRACT

An ultrasonic probe suitable for reducing reflected waves returning from a rear surface part to a transducer side, and an ultrasonic diagnostic apparatus. Ultrasonic probe 1 comprises transducer 10 transmitting and receiving ultrasonic waves to and from a subject, a backing material 12 disposed on the rear side of the transducer 10, and heat dissipating block 14 stacked on the backside of the backing material 12. At least one of the backing material 12 and heat-dissipating block 14 comprises void 16 therein. A sound absorbing material 18 is desirably filled in void 16.

20 Claims, 11 Drawing Sheets

FOREIGN PATENT DOCUMENTS

| | | |
|---|---|---|
| JP | 96-268238 | 11/1986 |
| JP | 63-140880 | 6/1988 |
| JP | 01-293851 A | 11/1989 |
| JP | 02-06131 U * | 5/1990 |
| JP | 2-061312 U | 5/1990 |
| JP | 05-244690 A | 9/1993 |
| JP | 09-010216 | 1/1997 |
| JP | 2000-184497 | 6/2000 |
| JP | 2004-329495 | 11/2004 |

* cited by examiner (A)

(B)

MAJOR AXIS
DIRECTION

ULTRASONIC PROBE AND ULTRASONIC DIAGNOSIS APPARATUS

TECHNICAL FIELD

The present invention relates to an ultrasonic probe in which transducers are arranged for transmitting and receiving ultrasonic waves between an object to be examined, and an ultrasonic diagnostic apparatus for constructing an ultrasonic image as a diagnostic image of the object.

BACKGROUND ART

An ultrasonic diagnostic apparatus is for providing driving signals to an ultrasonic probe, and for reconstructing an ultrasonic image based on the receiving signal outputted from the ultrasonic probe. An ultrasonic probe is for converting the driving signals into ultrasonic waves and transmitting them to the object, and has transducers arranged therein which are for receiving the reflected echo signals generated from the object and converting them into the receiving signals.

In an ultrasonic probe, upon transmitting ultrasonic waves from the transducers to the object, ultrasonic waves are effused also to the backside of the probe. Given this factor, a backside section is disposed on the backside of the transducer. For example, the backside section has a backing layer disposed on the backside of the transducer and a heat-dissipating member laminated on the backside of the backing layer, causes the backing layer to attenuate the ultrasonic waves effused to the backside of the transducer, and discharges the heat built up in the backing layer due to the attenuation to the outside via the heat-dissipating member (for example, refer to Patent Document 1).

However, there are cases that the incoming ultrasonic waves from the transducer to the backside return to the transducer side by reflecting at the backside, especially at the bonded surface of the backing layer and the heat-dissipating member. Such reflected waves could lead to deterioration of S/N (Signal to Noise) of ultrasonic images, and also to increase of surface temperature of the ultrasonic probe.

Given this factor, in Patent Document 1, reduction of noise is carried out by changing figuration of the bonded surface of the backing layer and the heat-dissipating member to the minor axis direction of the transducer, and dispersing the reflected waves being reflected at the bonded surface and returned to the transducer side.

Patent Document 1: JP-A-2004-329495

DISCLOSURE OF THE INVENTION

Problems to be Solved

However, in the method for changing the bonded surface of the backing layer and the heat-dissipating member in the minor axis direction of the transducer described in Patent Document 1, the possibility remains that a part of the dispersed reflected waves return to the transducer side, and as for the reduction of the reflected waves, there still remains room for further improvement.

Or, in a method as seen in Patent Document 1, another possibility for sufficiently attenuating ultrasonic waves effused from the transducer to the heat-dissipating member is to make the backing layer thicker. However, whereas the ultrasonic waves can be attenuated using the backing layer, thermal resistance increases in proportion to the thickness of the backing layer whereby increasing heat storage therein. As a result, the heat stored in the backing layer can easily be carried to the transducer side, which lowers sensitivity of the ultrasonic probe and leads to the increase of surface temperature, thus thickening of the backing layer is not preferable.

The objective of the present invention is to provide an ultrasonic probe that effectively reduces the reflected waves returning from the backside of the probe to the transducer side.

Means to Solve the Problem

In order to achieve the above-mentioned objective, the ultrasonic probe of the present invention comprises:
 a transducer for transmitting/receiving ultrasonic waves to/from an object to be examined; and
 a backside section disposed on the backside of the transducer,
 wherein the backside section has:
 a first attenuation section disposed on the backside of the transducer, and attenuates the ultrasonic waves effused from the transducer; and
 a heat-dissipating section for dissipating the heat from the first attenuation section,
 characterized in that the backside section has a second attenuation section for further attenuating the ultrasonic waves effused from the transducer.

Also, in order to solve the above-mentioned problems, the ultrasonic diagnostic apparatus of the present invention is characterized in comprising the ultrasonic probe as mentioned above.

By such configuration, ultrasonic waves effused from the transducer to the backside are attenuated in the first attenuation section, and receives further attenuation in the second attenuation section, whereby attenuating a majority of the incoming ultrasonic waves to the backside. Through this effect, the reflected waves returning from the backside of the probe to the transducer side can be effectively reduced.

Particularly, when the backing layer as the first attenuation section being disposed on the backside of the transducer and the heat-dissipating section disposed on the backside of the backing section are provided as the backside section, the second attenuation section is formed in the backing layer and/or the heat-dissipating section.

By such configuration, a majority of incoming ultrasonic waves on the backing layer and the second attenuation section are attenuated, and both effects for restraining increase of temperature of the probe on the body surface of the object and lowering the reflected waves being the base of noise can be attained, even when thickness of the backing layer is reduced.

Also, when the second attenuation section is formed in the backing layer being the first attenuation section, it is desirable that the second attenuation section is formed so that the position of the end surface of the second attenuation section on the transducer side falls on the position apart from the surface on the transducer side of the backing layer by an integral multiplication of the wavelength of the ultrasonic wave in vertical direction to the backside of the transducer. Or, when the second attenuation section is formed in the heat-dissipating section, it is desirable that the second attenuation section is formed so that the position of the end surface of the second attenuation section on the transducer side falls on the position apart from the bonded surface of the backing layer and the heat-dissipating section by an integral multiplication of the wavelength of the ultrasonic wave in vertical direction to the backside of the transducer. By such formation of the second attenuation section, acoustic impedance equivalent to thickness of an integral multiplication of the wavelength of the ultrasonic wave can be made approximately zero, and the reflected waves returning from the backside section to the transducer side can be further constrained.

The second attenuation section is desirably formed having a void, and the void may be filled in with a sound absorbing material. By such configuration, effect for attenuating noise that appears on an ultrasound image can be further improved.

As mentioned above, the present invention can provide an ultrasonic probe having improved effect on reducing the reflected waves returning from the backside to the transducer side, and an ultrasonic diagnostic apparatus having improved effect on reducing noise appearing on an ultrasound image.

BEST MODE FOR CARRYING OUT THE INVENTION

The First Embodiment

The first embodiment of the ultrasonic probe to which the present invention is applied will be described referring to the diagrams. FIG. 1A is a diagram showing a cross section in axis direction of the ultrasonic probe of the present embodiment, viewing from major axis direction. FIG. 1B is a diagram showing a heat-dissipating block of FIG. 1A viewing from major axis direction (direction of arrow X shown in the diagram).

As shown in FIG. 1A and FIG. 1B, ultrasonic probe 1 to use for imaging an ultrasound image of the object comprises transducer 10 for transmitting/receiving ultrasonic waves between the object and the backside section imposed on the backside of the transducer. The backside section has backing material 12 as the backing layer (the first attenuation section) imposed on the backside of transducer 10 and heat-dissipating block 14 as the heat-dissipating section laminated on the backside of backing material 12. Ultrasonic probe 1 is stored in the probe case.

Ultrasonic probe 1 has void 16 formed in heat-dissipating block 14 as the second attenuation section as shown in FIG. 1B, and sound absorbing material (that is the material for absorbing and attenuating ultrasonic waves) 18 is filled in void 16. Heat-dissipating block 14 is formed with a material having high thermal conductivity (for example, a metal such as aluminum) As for the material for sound absorbing material 18, natural material or synthetic material having comparatively large rate of decrease such as silicon or epoxide resin is used.

Further, ultrasonic probe 1 will be described. Transducer 10 has a plurality of piezoelectric elements being arranged therein for transmitting/receiving ultrasonic waves between the object. For the sake of convenience, the array direction of the piezoelectric elements will be referred to as major axis direction, and direction orthogonal to major axis direction will be referred to as minor axis direction. Also, the side of the surface of transducer 10 for transmitting/receiving ultrasonic waves will be arbitrarily referred to as an object side, and the opposite surface side thereof will be referred to as the back surface side.

On the object side of transducer 10, acoustic commensurate layer 22 is laminated intervening electrode 20a in between. Acoustic lends 24 is disposed on the object side of acoustic commensurate layer 22. Acoustic commensurate layer 22 is formed with material having acoustic impedance of, for example, in the middle of transducer 10 and the object, and effectively transmits ultrasonic waves transmitted from transducer 10 into the object. Acoustic lends 24 has a convex surface for focusing ultrasonic waves.

Meanwhile, backing material 12 is disposed on the backside of transducer 10 intervening electrode 20b in between.

Backing material 12 is for absorbing ultrasonic waves transmitted from transducer 10 to the backside. Heat-dissipating block 14 has bonded section 14a being bonded to the backside of backing material 12 and extended section 14b which is a board shape and is extended from bonded section 14a in backside direction (direction of arrow Y in the diagram) Bonded section 14a is formed so that the cross-sectional area of the side connecting to extended section 14b in minor axis direction is being reduced as proceeding toward extended section 14b. In other words, the backside of bonded section 14a on the side connecting to extended section 14b is slanted in minor axis direction. Extended section 14b is formed so that the width in minor direction becomes smaller than bonded section 14a and that the width in major direction becomes the same as bonded section 14a, corresponding to the gripper of the probe case.

In heat-dissipating block 14, void 16 is formed inside of extended section 14b. Void 16 is formed in the position apart from the surface on the side of transducer 10 of heat-dissipating block 14 (that is the bonded surface of backing material 12 and heat-dissipating block 14) by integer n-times of the wavelength $\lambda$ of the ultrasonic wave, in the thickness direction (direction of arrow Y in the diagram). In this case, as will be described later, acoustic impedance of the part equivalent to the thickness can be made approximately zero, and the reflected waves returning from the backside to the transducer side can be constrained more effectively.

As for the method for forming void 16, cutting work such as drilling can be applied. Formed void 16 passes through extended section 14b in minor direction, and is zoned into two flat surfaces parallel to minor axis direction and the rounded surface connecting the respective surfaces thereof. Meantime, void 16 can be formed at a part in minor axis direction without passing through in minor axis direction. Distance S between the flat surface which zones void 16 and the sidewall of heat-dissipating block 14 is designed as, for example, 7 mm. Also, rounded surface 26 of void 16 on the side closer to backing material 12 has the bending radius of, for example, 8 mm and is distended to the side of transducer 10. The rounded surface on the side farther from backing material 12 has the bending radius of, for example, 8 mm and is distended in backside direction (direction of arrow Y in the diagram). And length in backside direction of void 16 is designed as, for example, 20 mm. Void 16 may be formed plurally by arranging them in major or minor direction. Also, void 16 can be formed in bonded section 14a of heat-dissipating section 14 by making integer-n a small number. Or, on the contrary, void 16 may be formed at the back of extended section 14b of heat-dissipating block 14 by making integer-n a big number.

And void 16 of the present embodiment is filled with sound absorbing material 18. As for the material of sound absorbing material 18, while natural material or synthetic material such as silicon or epoxide resin having comparatively large rate of decrease may be used, it is preferable to use the material having approximately the same acoustic impedance as the one of backing material 12.

When drive signals are provided to such configured ultrasonic probe 1, the provided drive signals are applied to transducer 10 via electrodes 20a and 20b. The applied drive signals are converted into ultrasonic waves by transducer 10 and transmitted to the object. The reflected echo generated from the object is received by transducer 10. The received reflected echo is converted into a reception signal as an electronic signal, and outputted from the ultrasonic probe. An ultrasound image is thus constructed by the ultrasonic diagnosis apparatus based on the outputted reception signals.

In such ultrasonic probe 1, when ultrasonic waves are transmitted to the object from transducer 10, the ultrasonic waves are effused also on the backside of transducer 10. Most of the effused ultrasonic waves are attenuated at backing material 12. The ultrasonic waves passed through backing material 12 without being attenuated enter in heat-dissipating block 14.

In accordance with the present embodiment, since difference between acoustic impedance of sound absorbing material 18 and acoustic impedance of heat-dissipating block 14 is comparatively small, most of the incoming ultrasonic waves to heat-dissipating block 14 enter into sound absorbing material 18 and get attenuated. Accordingly, reflected waves returning from heat-dissipating block 14 to transducer 10 side can be reduced.

In particular, according to the present embodiment, it is possible to reduce the reflected waves returning from heat-dissipating block 14 without increasing the thickness of backing material 12, that is, with the usage of thin backing material 12. Therefore, the effect for both restraining increase of surface temperature of acoustic lends 24 and reducing the reflected waves causing noise can be attained. As a result, since energy of drive signals to be provided to transducer 10 can be increased, ultrasonic waves can be emitted to comparatively deep portions of the object, and image quality of the ultrasound images can be improved.

Also, as to heat-dissipating block 14, since thickness L from the surface on the side of transducer 10 (that is the bonded surface of backing material 12 and heat-dissipating block 14) to void 16 is integer n-times of the wavelength λ of ultrasonic waves, acoustic impedance of the part equivalent to the thickness becomes zero. Therefore, noise due to the reflected waves returning from heat-dissipating block 14 can be restrained.

Also, as seen in FIG. 1A and FIG. 1B, even when void 16 is formed, the contact area of heat-dissipating block 14 and backing material 12 does not change, and heat transmits from backing material 12 to heat-dissipating block 14 via contact surface thereof. The transmitted heat runs through the portions such as between the sidewall of heat-dissipating block 14 and the flat surface of void 16, then is discharged to the outside from the surface of heat-dissipating block 14. Since the communication channel of heat is secured in this way, it is possible to avoid degradation of discharge characteristics of heat-dissipating block 14, whereby restraining the increase of surface temperature of acoustic lends 24.

FIG. 2 is a block diagram of ultrasonic diagnostic apparatus 2 to which ultrasonic probe 1 is connected. Ultrasonic diagnostic apparatus 2 comprises:

transmission/reception unit 30 for providing drive signals to ultrasonic probe 1 and processing the reception signals outputted from ultrasonic probe 1;

phasing addition unit 32 for phasing and adding the reception signals outputted from transmission/reception unit 30;

image constructing unit 34 for reconstructing an ultrasound image based on the reception signals outputted from the phasing addition unit 32; and display unit 36 for displaying an ultrasound image outputted from image constructing unit 34.

FIG. 3 is a display example for verifying the effect of the present embodiment. For the sake of convenience, the diagram is illustrated with a focus on the noise appears on the ultrasound image. FIG. 3A is a display example upon imaging a heart. As seen in FIG. 3A, ultrasound image 39 and ultrasound image 41 are displayed side by side. Ultrasound image 39 is an image created using a prior and existing ultrasonic probe. Ultrasound image 41 is an image created using ultrasonic probe 1 of the present embodiment. Also, in the present example, silicon with 0.81 dB/mm of rate of decrease is used. As seen in FIG. 3A, noise is effectively reduced in ultrasound image 41 compared to ultrasound image 39. Also, it was verified that the surface temperature of acoustic lends 24 was not increased even after 2.5 hours passed since the start time of imaging.

FIG. 3B is a display example upon imaging a skull bone. Ultrasound image 43 being imaged using the prior and existing ultrasonic probe is displayed on the left side, and ultrasound image 45 being imaged using ultrasonic probe 1 of the present embodiment is displayed on the right side. In the same manner as FIG. 3A, noise is effectively reduced in ultrasound image 45 compared to ultrasound image 43.

Furthermore, as for sound absorbing material 18, the same result could be obtained with the usage of epoxy (trade name: Epicoat 807, manufacturer: Yuka-Shell Epoxy Co., Ltd.), tungsten (trade name: W-2, manufacturer: Japan New Metals Co., Ltd.), admixture of epoxy and tungsten (mixing ratio 16 g:57 g, rate of decrease 1.13 dB), and Achmex (trade name: Achmex R-11, manufacturer: Nihon Gosei Kako Co., Ltd., rate of decrease: 2.94 dB/mm). Rate of decrease mentioned here indicates the rate that ultrasonic waves of 2 MHz frequency in a circumstance of normal temperature 25° C. decreases. Epicoat and Achmex mentioned here are registered trademarks.

While the present invention is described above by the first embodiment, it should not be taken by way of limitation. For example, while an example of disposing backing material 12 and heat-dissipating block 14 as the backside section is described, only one of the two may be disposed instead for applying the present invention. In that case, void 16 can be formed in either backing material 12 or heat-dissipating block 14, and sound absorbing material 18 can be filled in the void 16.

As mentioned above, in accordance with the present embodiment, the reflected waves returning from heat-dissipating block 14 to transducer 10 side can be restrained and S/N of images can be improved, by forming void 16 of predetermined size at a predetermined distance from the surface of backing material 12 side of heat-dissipating block 14 and filling sound absorbing material 18 in the void 16. Furthermore, since thickness of backing material 12 can be made small, degradation of transmitting/receiving sensitivity of transducer 10 can be reduced and increase of surface temperature of acoustic lends 24 can be restrained.

Here, additional description will be made regarding position of void 16. FIG. 4 is a diagram for illustrating position of the void, and is for use in acoustic analysis of 4 terminal networks to be used for electric circuit analysis.

As seen in FIG. 4, backing material 46 is connected to the terminal I side of heat-dissipating section 47 via a pair of end terminals. In heat-dissipating block section 47, the side of terminal II is connected to sound absorbing material section 48 via a pair of end terminals. A, B, C and D in the diagram are comparable to 4 terminal constant of the electric network theory. $Z_B$ denotes acoustic impedance of backing material section 46. $Z_r$ denotes acoustic impedance of heat-dissipating block section 47. $Z_X$ denotes acoustic impedance of the sound absorbing material. $E_1$ and $E_2$ are comparable to power voltage of the electric network theory, and $I_1$ and $I_2$ are comparable to electric current.

In such 4 terminal network, impedance $Z_{i1}$ can be represented as formula 1. Also, in the case that a material of which the rate of decrease is small is used for heat-dissipating block section 47, formula 1 is expressed as formula 2. Here, λ is the wavelength of the incoming ultrasonic wave to heat-dissipating block section 47. L is thickness of heat-dissipating block section 47 intervened between backing material section 46 and sound absorbing material section 48, which is comparable to the distance, in case of FIG. 1, from the surface on the transducer 10 side of heat-dissipating block 14 to void 16 in the thickness direction.

$$Z_{i1} = \frac{E_1}{I_1} = (AZ_x + B)/(CZ_x + D) \quad \text{[Formula 1]}$$

$$Z_{i1} = \frac{\cos\frac{2\pi}{\lambda}L \cdot Z_x + Z_r j\sin\frac{2\pi}{\lambda}L}{(Z_x/Z_r)j\sin\frac{2\pi}{\lambda}L + \cos\frac{2\pi}{\lambda}L} \quad \text{[Formula 2]}$$

In the same manner, impedance $Z_{i2}$ of heat dissipating block section 47 viewing from terminal II side is expressed as formula 3. Also, in the case of using a material having a small rate of decrease for heat-dissipating block section 47, formula 3 is expressed as formula 4.

$$Z_{i2} = \frac{E_2}{I_2} = (DZ_B + B)/(CZ_B + A) \quad \text{[Formula 3]}$$

$$Z_{i2} = \frac{\cos\frac{2\pi}{\lambda}L \cdot Z_B + Z_r j\sin\frac{2\pi}{\lambda}L}{-(Z_B/Z_r)j\sin\frac{2\pi}{\lambda}L + \cos\frac{2\pi}{\lambda}L} \quad \text{[Formula 4]}$$

When L=λ in formula 2 and formula 3, impedance $Z_{i1}$ is expressed as formula 5. Also, impedance $Z_{i2}$ is expressed as formula 6.

$$Z_{i1} = Z_x \quad \text{[Formula 5]}$$

$$Z_{i2} = Z_B \quad \text{[Formula 6]}$$

As evidenced by formulas 5 and 6, when L=nλ, from backing material section 46, impedance of heat-dissipating block section 47 turns out to be the same as impedance $Z_X$ of sound absorbing material section 48. In the same manner, from sound absorbing material section 48, impedance of heat-dissipating block section 47 turns out to be the same as impedance $Z_B$ of backing material section 46. In other words, when thickness L from the surface on transducer 10 side of heat-dissipating block 14 in FIG. 1 to void 16 in the thickness direction is integer n-times of the wavelength λ of the ultrasonic wave, acoustic impedance of the part equivalent to the thickness L looks as zero, thus noise due to reflected waves returning from heat-dissipating block 14 can be reduced. Especially, when ZX=ZB, since difference between acoustic impedance on terminal I side of heat-dissipating block section 47 and acoustic impedance on terminal II side becomes zero, noise due to reflected waves can be reduced even more efficiently.

Second Embodiment

A second embodiment of the ultrasonic probe to which the present invention is applied will be described referring to FIG. 5. The present embodiment is different, in the point of using a triple layered heat-dissipating section, from the first embodiment using the heat-dissipating block in which the void is formed. Therefore, points of difference will be mainly described, by using the same symbols for the places relatively corresponding to the first embodiment.

FIG. 5 is a diagram showing a cross section in axis direction of ultrasonic probe of the present embodiment 1b, viewing from minor axis direction. As shown in FIG. 5, in ultrasonic probe 1b, a triple layered heat-dissipating section is disposed in the backside of backing material 12. The heat-dissipating section has heat-dissipating member 51 as the first heat-dissipating layer disposed on the backside of backing material 12, sound absorbing material 52 as the sound-absorbing layer laminated on the backside of heat-dissipating member 51, and heat-dissipating member 53 as the second heat-dissipating layer laminated on the backside of sound absorbing material 52. In other words, sound absorbing material 52 is sandwiched between heat-dissipating member 51 and heat-dissipating member 53. Heat-dissipating member 53 is formed having larger volume than heat-dissipating member 51. Also, material for heat-dissipating member 51 and heat-dissipating member 53 is the same as heat-dissipating block 14 of the first embodiment, which is a metal such as aluminum.

Also, support member 54 being extended along the sidewall of heat-dissipating member is disposed. One end side of support member 54 is fixed on the sidewall of heat-dissipating member 51 by a part such as a tuning peg, and other end side is fixed on the sidewall of heat-dissipating member 53 by a part such as a tuning peg. In other words, support member 54 is placed from heat-dissipating member 51 to heat-dissipating material 53 via sound absorbing material 52 along the sidewall. Support member 54 is formed by a material having heat transfer property such as aluminum, and operates as heat transfer channel. While two support members 54 are disposed in the example of FIG. 5, they can be increased as the need arises.

Thickness Ta of heat-dissipating member 51 needs to be an integral multiplication of the wavelength of the ultrasonic wave, and it is formed as, for example, 3.4 mm being the same as the wavelength of the ultrasonic wave in the example of FIG. 5. The ultrasonic wave mentioned here is the ultrasonic wave incoming to heat-dissipating member 51. For example, when center frequency of the incoming ultrasonic wave is 2 Mhz and acoustic velocity at heat-dissipating member 51 is 6800 m/sec, 1 wavelength of the ultrasonic wave would be 3.4 mm. Also, in sound absorbing material 52, while thickness Tb is formed as, for example, 5 mm, it can be determined as need arises.

In accordance with the present embodiment, since thickness Ta is small being the same as the wavelength of the ultrasonic wave, the ultrasonic wave incoming to heat-dissipating member 51 reaches sound absorbing material 52 passing through heat-dissipating member 51. Because of the above-mentioned effect, since the majority of ultrasonic waves are attenuated in sound absorbing member 52, the reflected waves returning from heat-dissipating member 51 to backing material 12 side are restrained and multiple noises can be reduced.

Also, the heat accumulated in heat-dissipating member 51 is conducted to heat-dissipating member 53 via support member 54. The conducted heat is effectively discharged to outside via support member 54, whereby restraining increase of surface temperature of acoustic lends 24.

The Third Embodiment

The third embodiment of the ultrasonic probe to which the present invention is applied will be described referring to FIG. 6. The present embodiment has the position and size of the void that are different from the first embodiment. Therefore, points of difference will be mainly described, by using the same symbols for the places relatively corresponding to the first embodiment.

FIG. 6 is a diagram showing a cross section in axis direction of ultrasonic probe 1c of the present invention, viewing from major axis direction. As shown in FIG. 6, in ultrasonic probe 1c, void 60 is formed in bonded section 14a of heat-dissipating block 14. Void 60 passes through bonded section 14a in major axis direction, and is zoned by two flat surfaces parallel to the backside of backing material 12 and a rounded surface connecting the respective flat surfaces. Void 60 also may be formed in a part of major axis direction without passing through in major axis direction. Distance Ua between the flat surfaces are designed as, for example, 5 mm. The rounded surface has bending radius of, for example, 2.5 mm and is distended to the wall side of bonded section 14a. In such void 60, sound absorbing material 62 is filled in. As for the material for sound absorbing material 62, it is the same as the one in the first embodiment.

Thickness Ub from the backside of backing material 12 (that is the bonded surface of backing material 12 and bonded section 14a) to the upper surface of void 60 (the end surface of the transducer side) needs to be an integral multiple of the wavelength of the ultrasonic wave, and is designed as, for example, 3.4 mm being the same as the wavelength of the ultrasonic wave, in the example of FIG. 6. Also, minimum thickness Uc from the rounded surface of void 60 to the sidewall of bonded section 14a is designed as, for example, 1 mm.

In accordance with the present embodiment, since thickness Ub is small being the same as the wavelength of the ultrasonic wave, the ultrasonic waves incoming from backing material 12 to bonded section 14a are mostly attenuated in sound absorbing material 62 of void 60 by passing though the part equivalent to thickness Ub. By this effect, the ultrasonic waves returning from heat-dissipating block 14 to the side of backing material 12 can be attenuated and multiple noises can be reduced.

Also, when heat of backing material 12 is transmitted to heat-dissipating block 14, the transmitted heat is conducted to the side of extended section 14b via places such as a part equivalent to thickness Uc. Since extended section 14b is formed having comparatively large area, heat can be effectively discharged to the outside from the surface area of extended section 14b. In other words, the part equivalent to thickness Uc operates as a heat transfer-channel, there is no need for disposing other members, whereby by simplifying the configuration of ultrasonic probe 1c.

FIG. 7 is a diagram showing a cross section in axis direction of ultrasonic probe 1d of another example of the present embodiment, viewing from minor axis direction. As seen in FIG. 7, a different point of ultrasonic probe id from the example in FIG. 6 is that void 70 passing through bonded section 14a in minor direction is formed in place of void 60 passing through bonded section 14a in major direction. Void 70 may be formed in a part in minor direction without passing through in minor direction. By such formation, the same effect as the example in FIG. 6 can be obtained.

FIG. 8A is a diagram showing the cross section in axis direction of ultrasonic probe 1e of another example of the present embodiment, viewing from major direction. FIG. 8B is a diagram viewing heat-dissipating block 14 of FIG. 8A from minor direction (direction of arrow X in the diagram).

As shown in FIG. 8, a different point of ultrasonic probe 1e from the example in FIG. 6 is that void 72 passing through bonded section 14a in minor direction is formed, in addition to void 60 passing through bonded section 14a in major axis direction. In other words, void 60 and void 72 are formed being orthogonal to each other. As shown in FIG. 8B, void 72 is designed with width W in major direction being, for example, 10 mm. According to the present embodiment, ultrasonic waves returning from heat-dissipating block 14 to the side of backing material 12 can be restrained more effectively.

While the present invention has been described through the third embodiment, it should not be taken in way of limitation. For example, shape of the bonded surface of backing material 12 and heat-dissipating block 14 can be variably formed, as shown in FIG. 7 FIG. 10 of Patent Document 1. In that case, the void need to be formed so that thickness Ub between the surface of bonded surface side of void 60 or void 72 and the bonded surface will be an integral multiplication of the wavelength of the ultrasonic wave, corresponding to the shape of the bonded surface.

The Fourth Embodiment

The fourth embodiment of the ultrasonic probe to which the present invention is applied will be described. The present embodiment is different in a point that the void is made hollow, from the first embodiment in which the void is filled with the sound absorbing material. Therefore, points of difference will be mainly described, by using the same symbols for the places relatively corresponding to the first embodiment.

The present embodiment will be described referring to FIG. 1.

In accordance with the present embodiment, since void 16 is made hollow as formed, difference of acoustic impedance between void 16 and heat-dissipating block 14 becomes comparatively large. Therefore, the incoming ultrasonic wave from backing material 12 to heat-dissipating block 14 is reflected to a different direction from incoming direction at round surface 26 that forms void 16, whereby enabling reduction of the reflected waves returning to the side of transducer 10.

Furthermore, the ultrasonic waves reflected at rounded surface 26 of void 16 repeat reflection at the boundary face of heat-dissipating block 14 or the surface of void 16. As a result, propagation path for the ultrasonic waves at heat-dissipating block 14 can be made longer than the thickness of heat-dissipating block 14. Therefore, since the ultrasonic wave is gradually attenuated in the process of being transmitted within heat-dissipating block 14, the reflected waves returning from heat-dissipating block 14 to the side of transducer 10 can be reduced, and noise can also be restrained.

Also, rounded surface 26 of void 16 does not have to be limited to the one of FIG. 1, and may take any shape. As long as it is formed so that at least a part of the surface on the side of transducer 10 of void 16 is not parallel to the bonded surface of the backside of transducer 10 or backing material 12 and heat-dissipating block 14, it can avoid the ultrasonic waves reflected at void 16 from directly returning to the side of transducer 10, whereby enabling the reduction of the reflected waves returning from the backside to the transducer side.

The Fifth Embodiment

The fifth embodiment of the ultrasonic probe to which the present invention is applied will be described referring to FIGS. 9 and 10. The present embodiment is different from the first embodiment in shape and number of the voids. Therefore, points of difference will be mainly described, by using the same symbols for the places relatively corresponding to the first embodiment.

FIG. 9A is a diagram showing a cross section in axis direction of ultrasonic probe 1f of the present embodiment, viewing from major axis direction. As shown in FIG. 9, in ultrasonic probe 1f, a plurality of voids 60 is formed in bonded section 14a of heat-dissipating block 14. Each void 60 passes through bonded section 14a in major axis direction, and is formed having a cross section that is approximately round shape. Diameter Ua of each cross-sectional shape is designed as, for example, 5 mm. And sound absorbing material 60 may be filled in at least one of the plurality of voids 60. FIG. 9A shows an example that all of the voids are filled with sound absorbing material 62. As for the material for sound absorbing material 62, it is the same as those in the first embodiment.

Each of the plurality of voids 60 is formed so that they have the same distance from the backside surface of backing material 12 (that is the bonded surface of backing surface 12 and bonded section 14a), and that thickness Ub from the backside of backing material 12 to the upper surface of the respective voids (end surface of the transducer side) will be an integral multiplication of the wavelength of the ultrasonic waves. In this example, the case that thickness Ub is set as, for example, 3.4 mm being the same as the wavelength of the ultrasonic wave is described. Also, a gap between minimum thickness Uc from the rounded surface of void 60 of both ends to the sidewall of bonded section 14a and the void is designed as, for example, 1 mm.

In accordance with the present embodiment, as with the previously mentioned effect in the third embodiment, since thickness Ub is small being the same as the wavelength of the ultrasonic wave, the incoming ultrasonic waves from backing material 12 to bonded section 14a passes through the part equivalent to thickness Ub, and vast majority of them are attenuated at sound absorbing material 62 of the respective voids 60. By this effect, the ultrasonic waves returning from heat-dissipating block 14 to the side of backing material 12 can be restrained, and multiple noises can be reduced.

Also, when heat of backing material 12 is transmitted to heat-dissipating block 14, the heat is carried to the side of extended section 14b via the part equivalent to thickness Uc and the gap portion of the respective voids. In other words, since the part equivalent to thickness Uc and the gap portion of the respective voids operate as the heat transfer channel, it is unnecessary to impose other members to operate as the heat transfer channel, whereby contributing to simplify the configuration of the ultrasonic probe 1f.

FIG. 9B is a diagram showing a cross section in axis direction of ultrasonic probe 1g of another example of the present embodiment, viewing from minor axis direction (direction of arrow X in the diagram). As shown in FIG. 9B, a point of ultrasonic probe 1g that is different from the example of FIG. 9A is that a plurality of voids 70 passing through bonded section 14a in minor axis direction is formed in place of the plurality of voids 60 passing through bonded section 14a in major axis direction. It is the same as FIG. 9A that the respective plurality of voids 70 may be formed to have the same distance from the backside of backing material 12 (that is the bonded surface of backing material 12 and bonded section 14a) It also is the same as FIG. 9A that at least one of such plurality of voids 70 is to be filled in with sound absorbing material 62. FIG. 9B indicates the example that all of the voids is filled in with sound absorbing material 62. As for the material of sound absorbing material 62, it is the same as those in embodiment 1.

Also, thickness Ub from the backside of backing material 12 to the upper surface of the plurality of voids 70, minimum thickness Uc from the rounded surface of the void of both ends to the sidewall of bonded section 14a, and concrete measurement of the gap between the voids are the same as the case of FIG. 9A. By such configuration, the same effect as the example in FIG. 9A can be attained.

While an example illustrated in the embodiment shown in FIG. 9 used the approximately round shape for the cross-sectional shape of the void, other shapes may be used without limiting to the round shape. An embodiment using another cross-sectional shape will be illustrated in FIG. 10.

FIG. 10A is a diagram showing a cross section in axis direction of ultrasonic probe 1j of another example of the present embodiment, viewing from major axis direction. FIG. 10B is a diagram showing a cross section of ultrasonic probe 1 k of another example of the present embodiment, viewing from minor axis direction (direction of arrow X in the diagram). In either example, a plurality of voids 60 and 70 having approximately triangle shape is formed in each probe, and adjacent voids have the inverted formation with respect to the backside direction (direction of arrow Y in the diagram).

Also, the respective plurality of voids 60 and 70 are formed to have the same distance from the backside of backing material 12 (that is the bonded surface of backing material 12 and bonded section 14a). Concrete measurement of the respective sections is the same as the case of FIG. 9, and thickness Ub from the backside of backing material 12 to the upper surface of the respective voids (end surface on the transducer side) is formed to be an integral multiplication of the wavelength of the ultrasonic wave. In this example, thickness Ub is designed as, for example, 3.4 mm being the same as the wavelength of the ultrasonic wave. Also, the gap between minimum thickness Uc from the apex of the void at both ends to the sidewall of bonded section 14a and the void is designed as, for example, 1 mm. With such configuration, the same effect as the example in FIG. 9 can be attained.

While an example is described in the above-mentioned embodiment 5 that the respective plurality of voids are formed having the same size and shape, at least two of the size and shape of the respective plurality of voids may be different. For example, voids having cross-sectional shapes such as approximately round or polygon may be formed in random order. In that case, what is necessary is that the upper surface of the plurality of voids (end surface on the transducer side) closest from the backside of backing material 12 (that is the bonded surface of backing material 12 and bonded section 14a) is formed along the surface parallel to the backside of backing material 12, and thickness Ub from the backside of backing material 12 to the upper surface of the plurality of voids (end surface on the transducer side) is formed to be an integral multiplication of the wavelength of the ultrasonic wave.

While the present invention have been described as above in the first fifth embodiments, it does not have to be limited to the above-mentioned embodiments.

For example, while the example is described that the surface for transmitting/receiving ultrasonic waves of transducer 10 has a rectangular shape, the present invention can also be applied to the surface having a circular shape. What is necessary for the present invention to be applied is that at least backing material 12 is imposed on the backside of transducer 10 as the backside section, and preferably that backing material 12 and heat-dissipating block 14a are imposed on the backside of transducer 10 as the backside section.

Also, condition such as disposing position, shape and number of the void does not have to be limited to the previously mentioned first~fifth embodiments, and embodiments described below are also applicable.

For example, a plurality of voids may be formed in longitudinal direction of heat-dissipating block 14 having intervals therebetween. The example thereof is illustrated in FIG. 11(A). FIG. 11(A) is a diagram showing a cross section in axis direction of the ultrasonic probe viewing from major axis direction, wherein only the backside is illustrated and the other portions are omitted. FIGS. 11(B)~(D) are illustrated in the same manner as FIG. 11 (A). FIG. 11 (A) is a diagram showing an example that a void with thickness Ua1 is formed leaving a void, from the backside of backing material 12, having thickness Ub1 which is an integral multiplication of the wavelength of the ultrasonic wave. A void with thickness Ua2 is further formed leaving a void having thickness Ub2 which is an integral multiplication of the wavelength of the ultrasonic wave, then a void with thickness Ua3 is formed leaving a void having thickness Ub3 which is multiplication of the wavelength of the ultrasonic wave, and a void with thickness Ua4 is formed leaving a void having thickness $n\lambda$ which is an integral multiplication of the wavelength of the ultrasonic wave. The respective voids may be filled with sound absorbing material. In addition, while 4 voids are formed in the example shown in FIG. 11 (A), the number of voids to be formed may be 2, 3 or more than 5.

Also, for example, the void may be formed straddling from bonded section 14a of heat-dissipating block 14 to extended section 14b. In other words, thickness of the void can be arbitrarily designed in a range that sufficient attenuation effect can be obtained. The example thereof is shown in FIG. 11(B). FIG. 11 (B) shows an example that the void is formed from bonded section 14a of heat-dissipating block 14 to extended section 14b. The void may be filled with an sound absorbing material.

Also, for example, the void may be formed in backing material 12. The example thereof is shown in FIG. 11(C). In an example of FIG. 11 (C), thickness Ub from the surface on the transducer 10 side of backing material 12 to the upper surface of the void (end surface on the transducer side) is designed to be an integral multiplication of the wavelength of the ultrasonic wave. And the void can be filled with an sound absorbing material. In accordance with this embodiment, majority of the incoming ultrasonic waves from the transducer to the backing material is attenuated at the sound absorbing material of the void after passing through the part equivalent to thickness Ub. By such configuration, ultrasonic waves returning to the transducer can be restrained, and multiple noises can be reduced.

Also, for example, the void may be formed in both backing material 12 and heat dissipating block 14. The example thereof is shown in FIG. 11(D). FIG. 11(D) shows an example that the void having thickness Ua1 is formed in backing material 12 by spacing, from the backside of transducer 10, thickness Ub1 which is an integral multiplication of the wavelength of the ultrasonic wave. The void having thickness Ua2 is further formed in heat-dissipating block 14 by spacing, from the backside of backing material 12, thickness Ub2 which is an integral multiplication of the wavelength of the ultrasonic wave. And the respective voids may be filled with an sound absorbing material.

The configuration may also be, for example, the arbitrary combination of the above-mentioned examples in FIG. 11 (A)~(D). Moreover, while the example is described that the void is formed in major direction of the ultrasonic probe in FIG. 11 (A)~(D), it may also be formed in minor axis direction in the same manner of the above-mentioned FIG. 11 (A)~(D).

In addition, shape of the void does not have to be limited to the ones shown in the examples in the above-mentioned FIGS. 11 (A)~(D), and one or more voids in different sizes having the cross sections in a shape of, for example, approximate circle, triangle or polygon as shown in FIGS. 9 and 10 may be formed.

BRIEF DESCRIPTION OF THE DIAGRAMS

DESCRIPTION OF THE SYMBOLS

Figure 1:
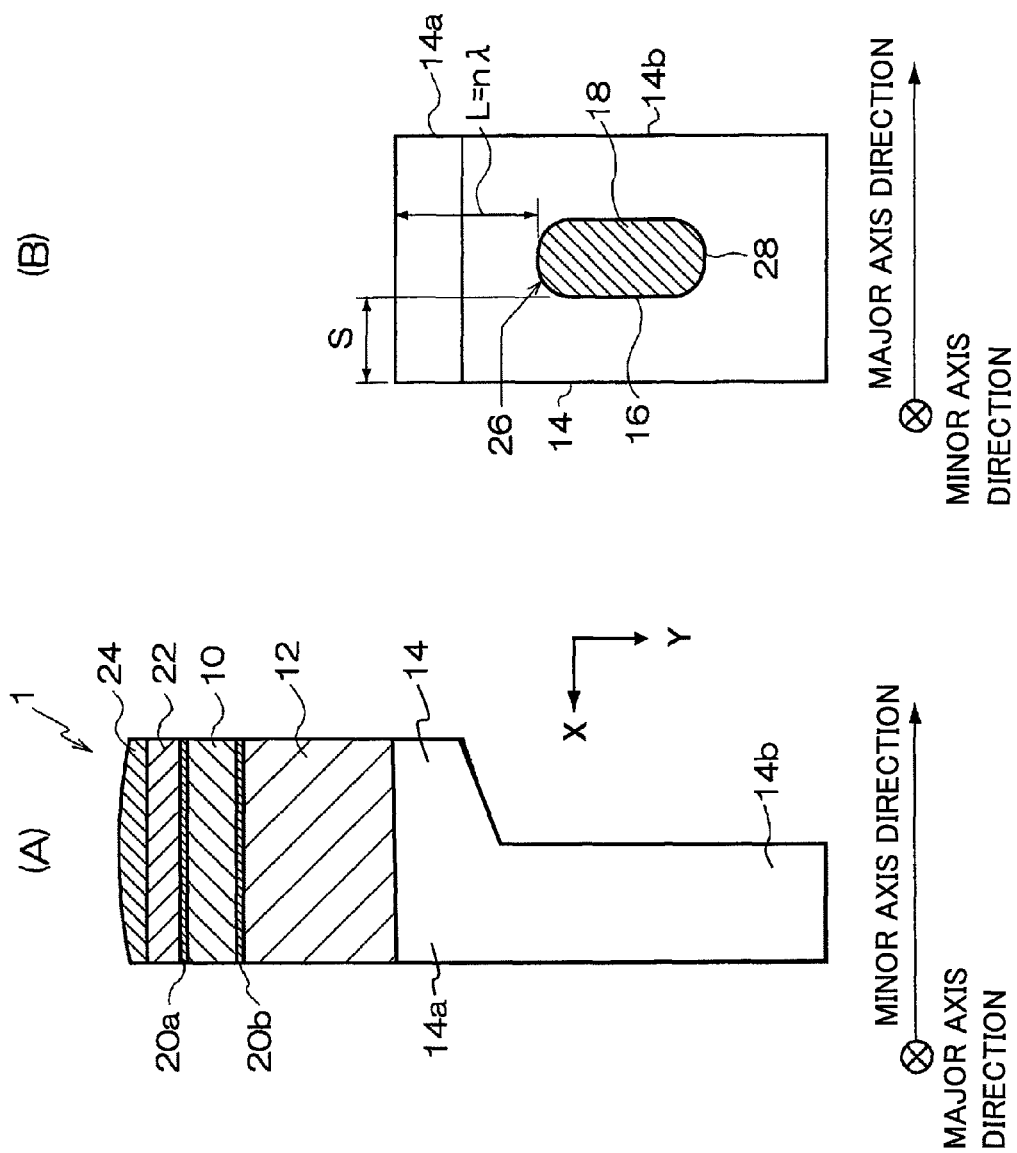
FIG. 1 is a block diagram showing an ultrasonic probe of the first embodiment to which the present invention is applied.
Figure 2:
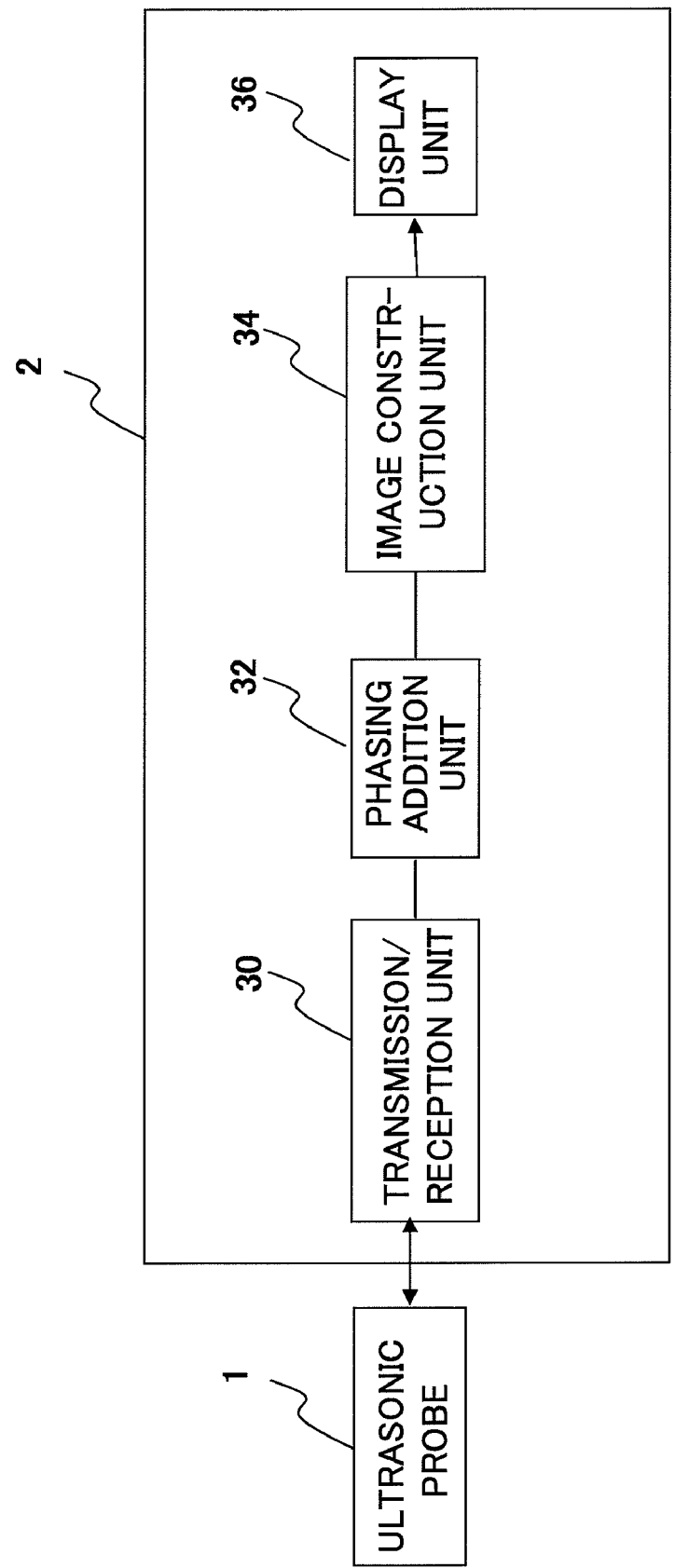
FIG. 2 is a block diagram showing an ultrasonic diagnostic apparatus to which the ultrasonic probe of FIG. 1 is connected.
Figure 3:
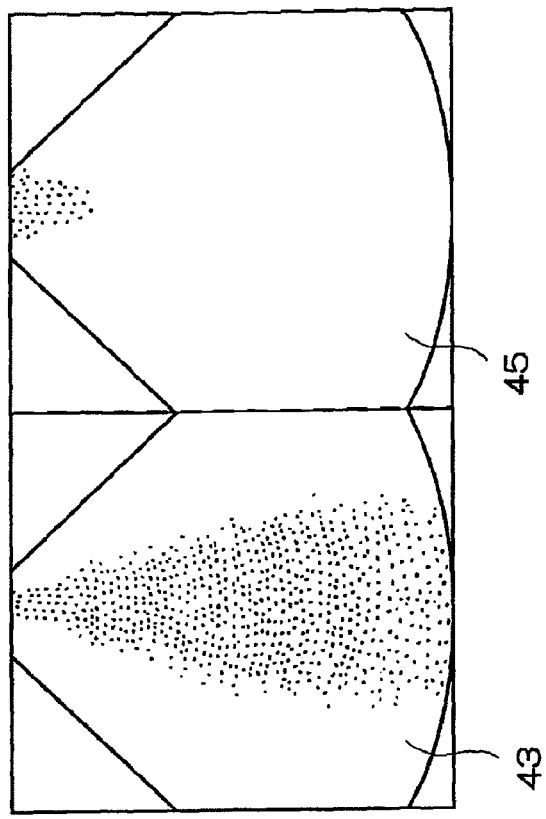
FIG. 3 is a display example of ultrasound images imaged by the ultrasonic diagnostic apparatus of FIG. 2.
Figure 3:
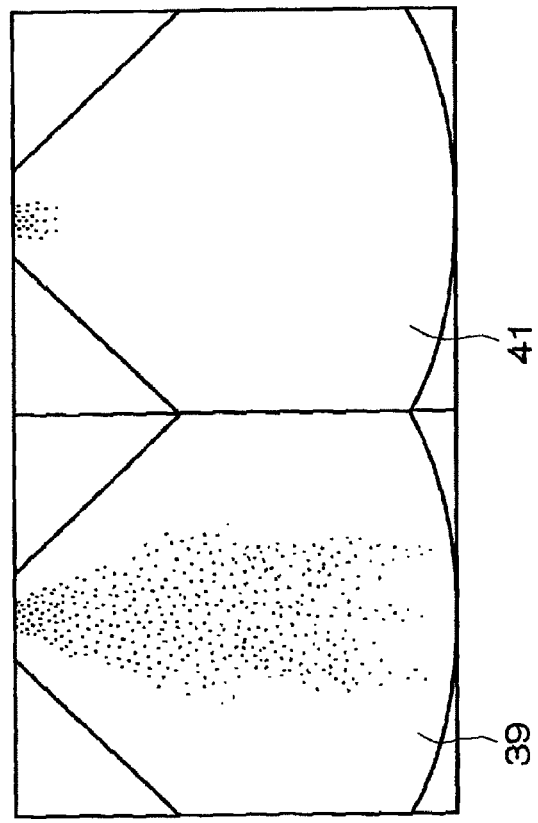
Figure 4:
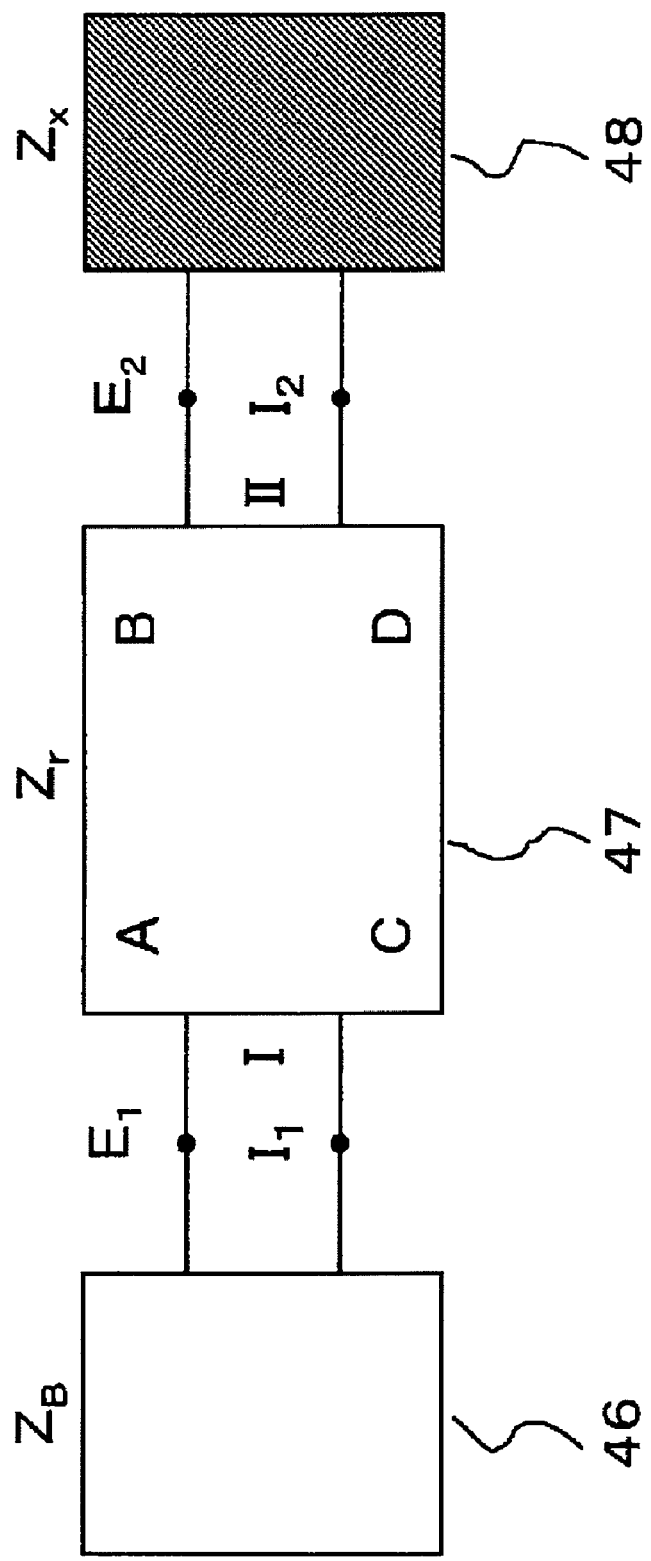
FIG. 4 is a diagram for illustrating the position of the void formed in the ultrasonic probe of FIG. 3.
Figure 5:
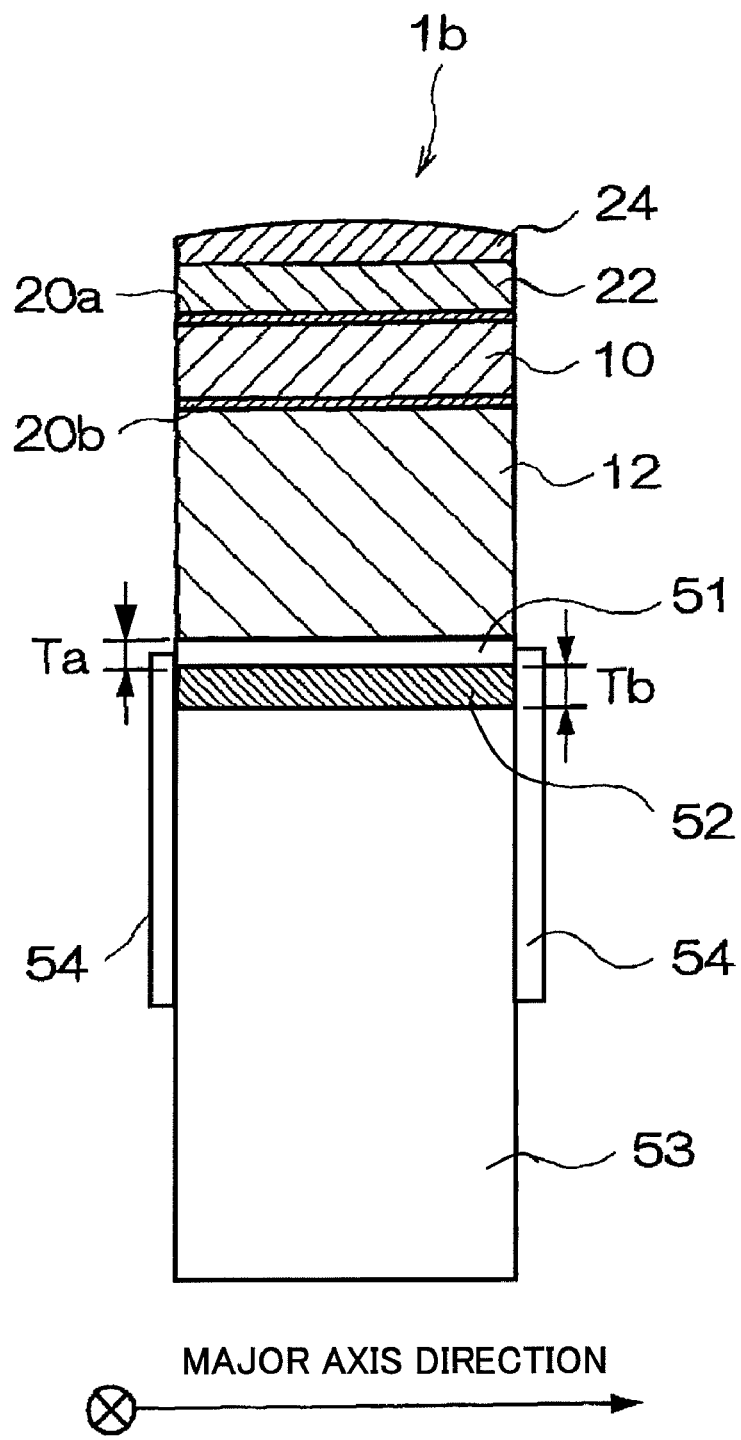
FIG. 5 is a block diagram showing the ultrasonic probe of the second embodiment to which the present invention is applied.
Figure 6:
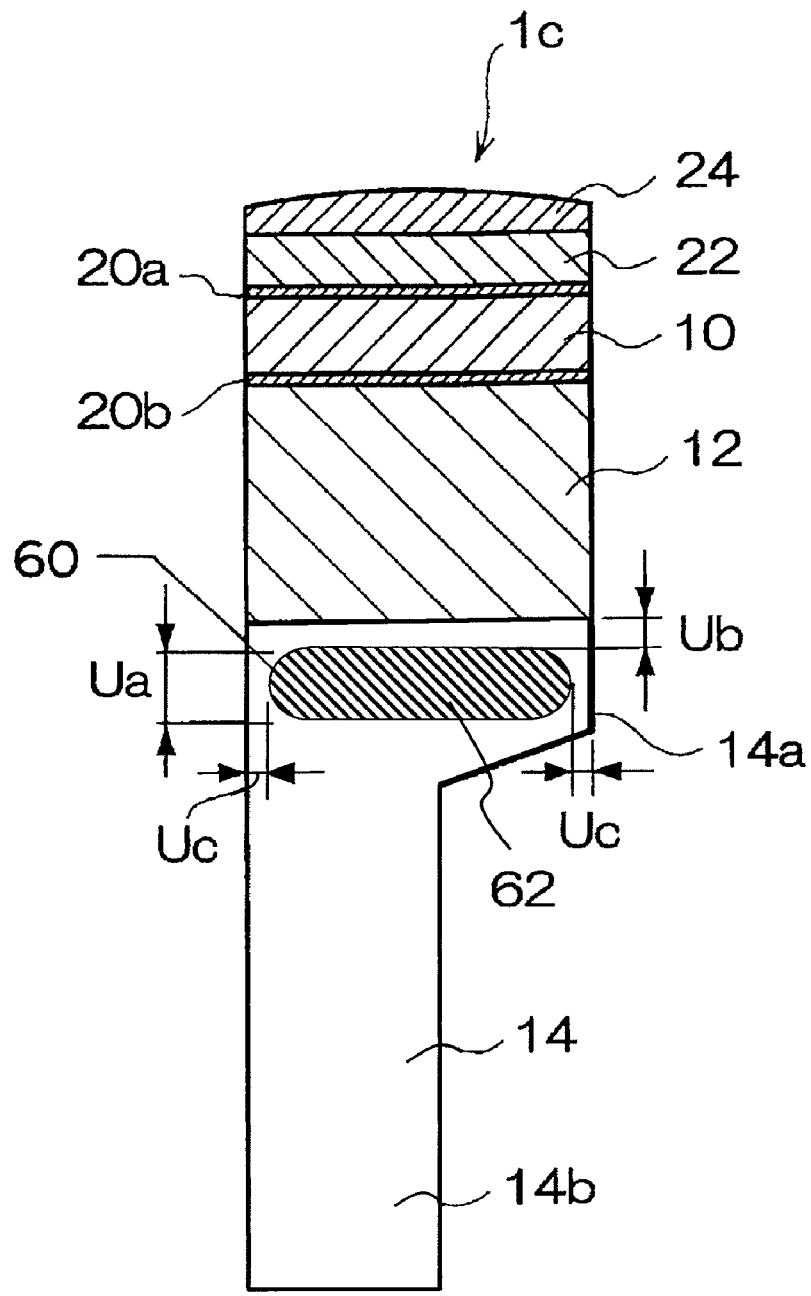
FIG. 6 is a block diagram showing the ultrasonic probe of the third embodiment to which the present invention is applied.
Figure 6:
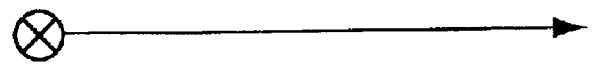
Figure 7:
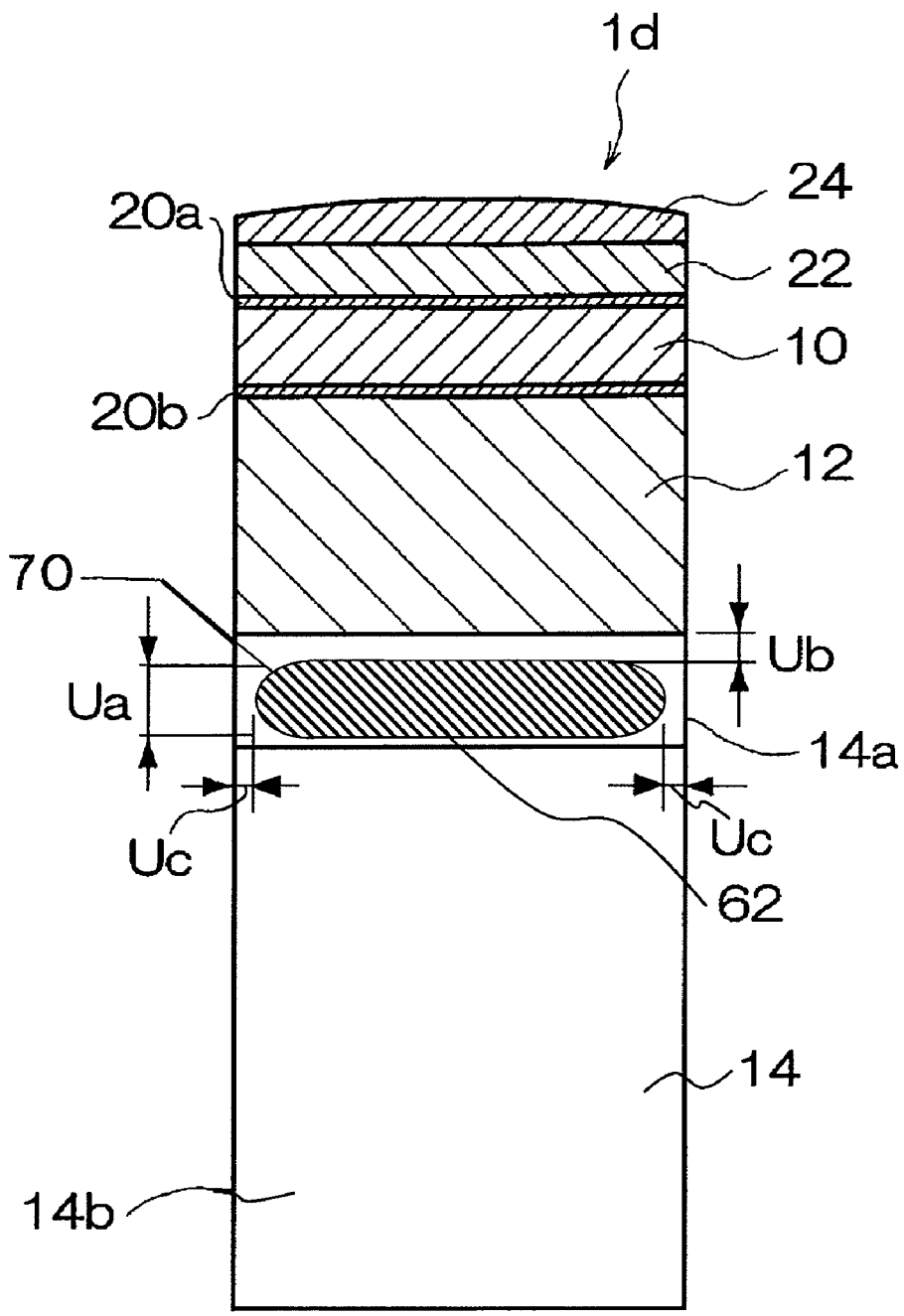
FIG. 7 is a block diagram showing a first other example of the ultrasonic probe in FIG. 6.
Figure 8:
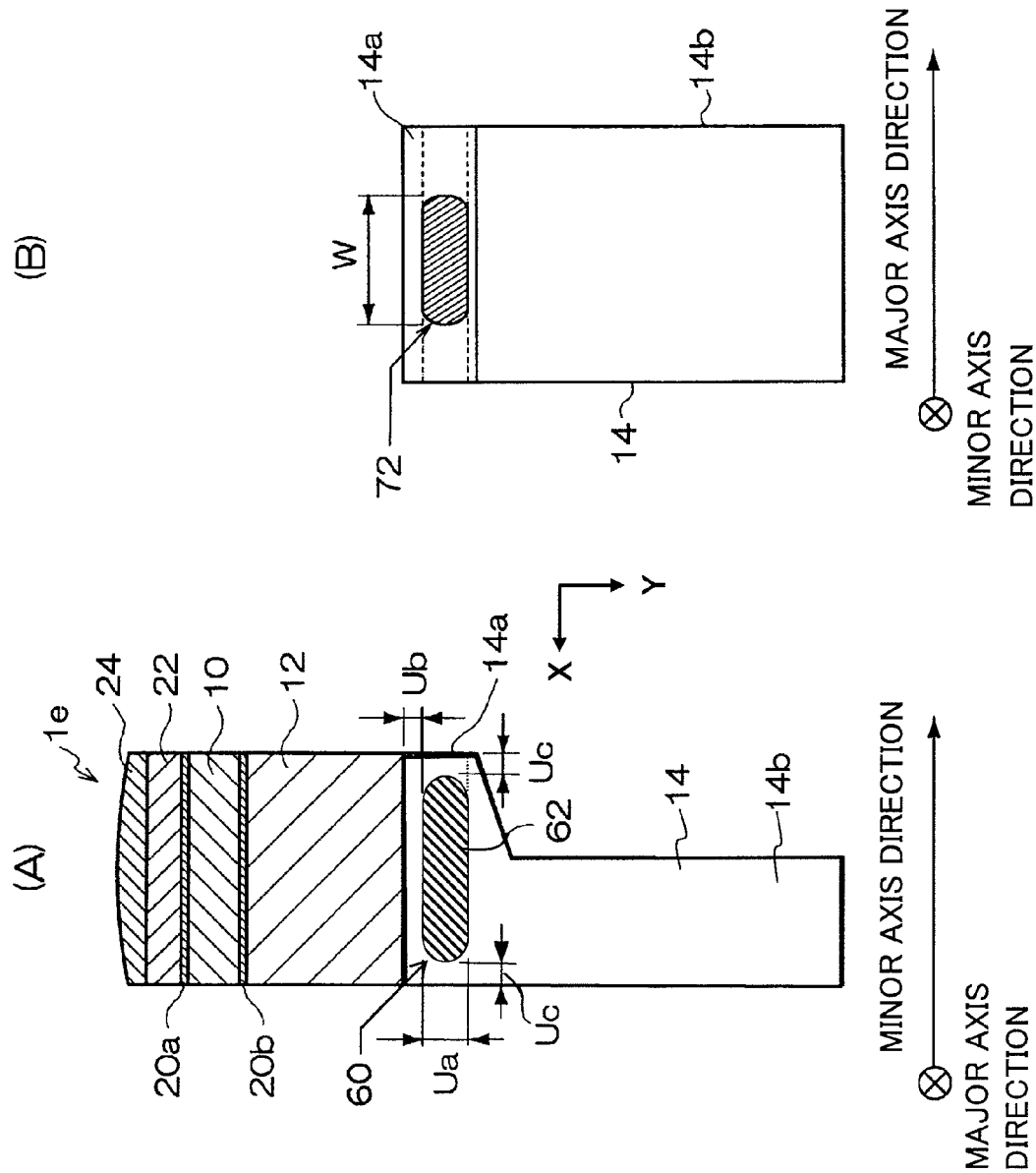
FIG. 8 is a block diagram showing a second other example of the ultrasonic probe in FIG. 6.
Figure 9:
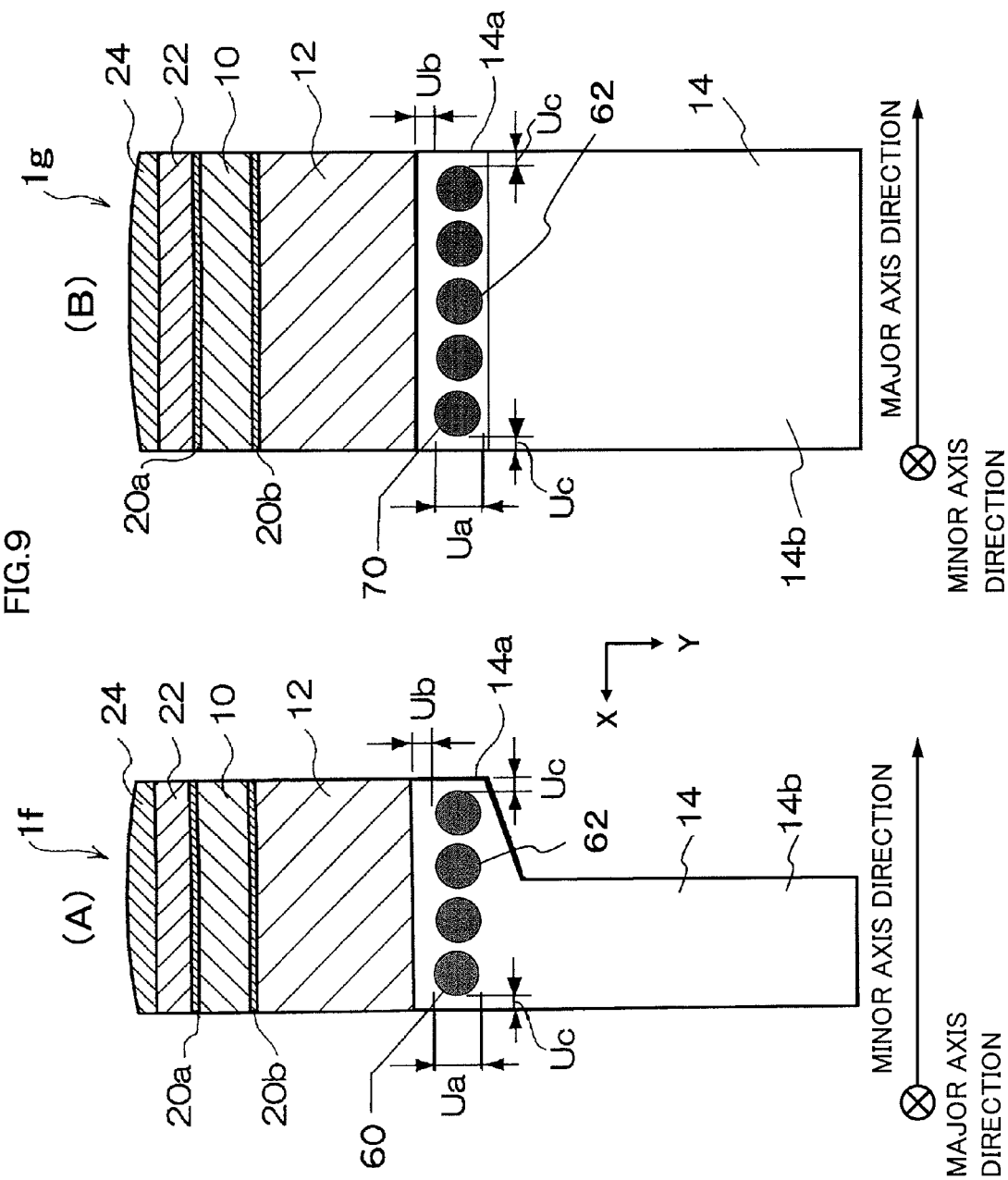
FIG. 9 is a block diagram showing an ultrasonic probe of the fifth embodiment to which the present invention is applied.
Figure 10:
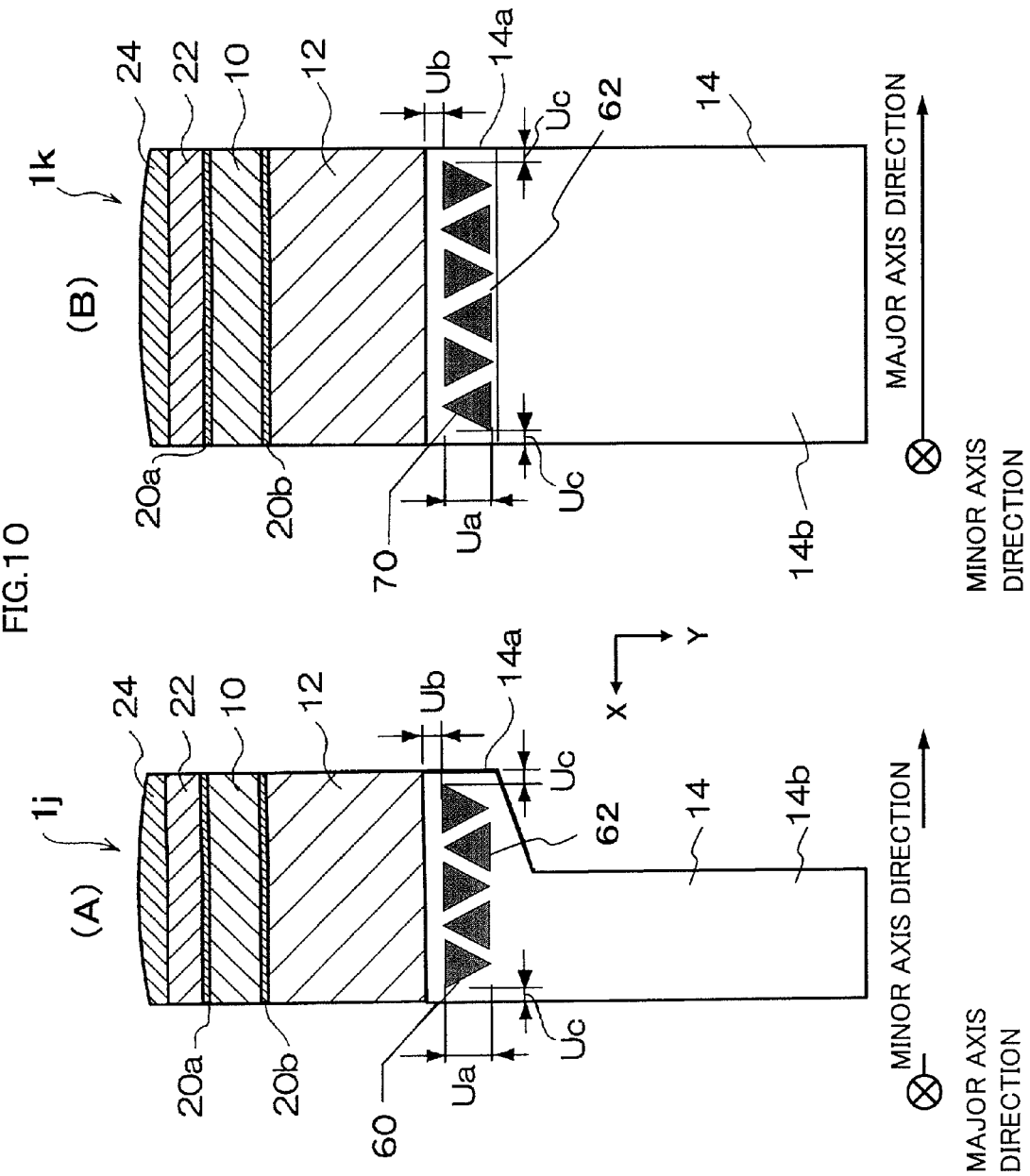
FIG. 10 is a block diagram showing another example of the ultrasonic probe in FIG. 9.
Figure 11:
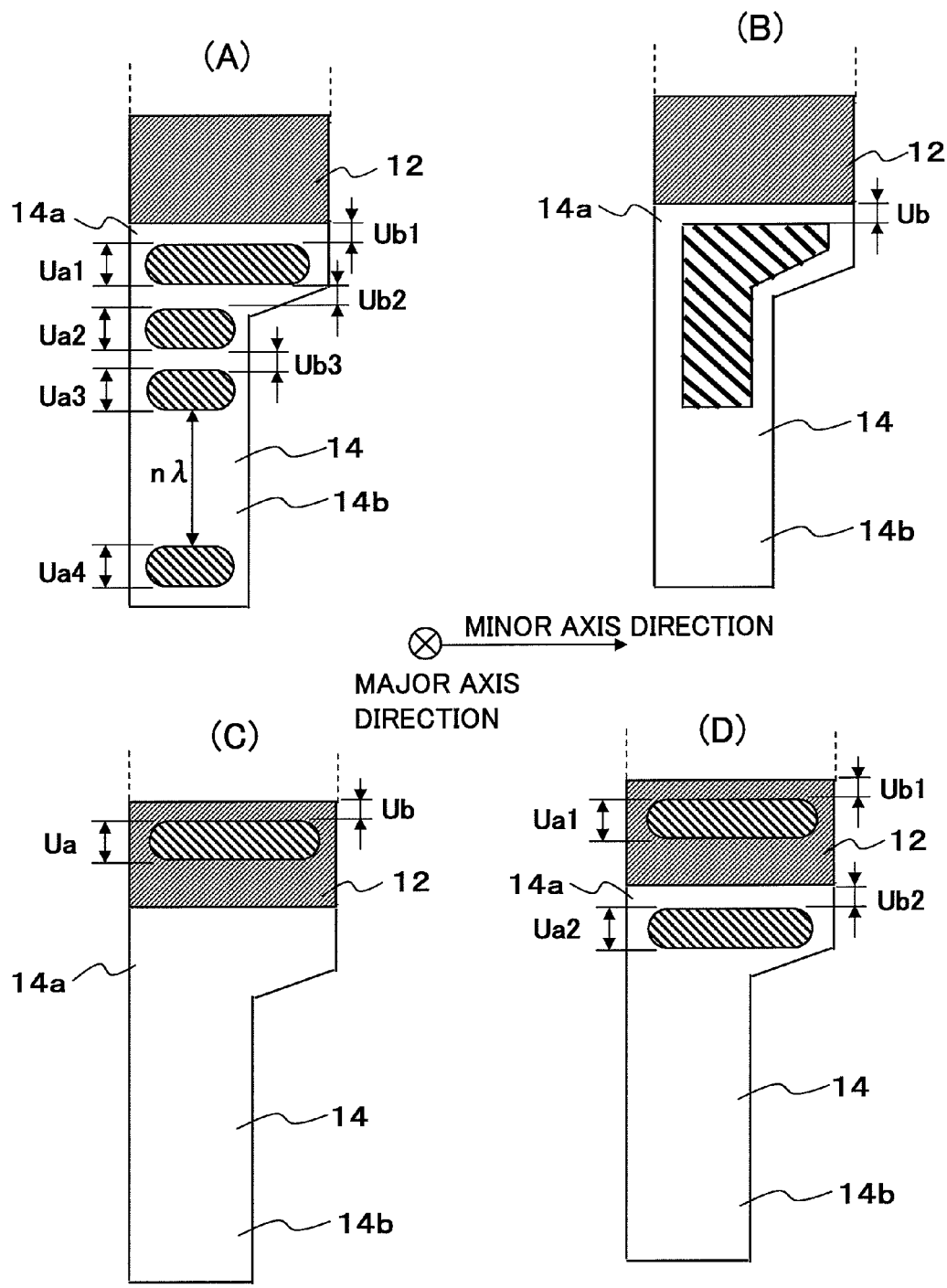
FIG. 11 is a diagram showing another example of the arrangement example of the voids.

1 . . . ultrasonic probe, 10 . . . transducer, 12 . . . backing material, 14 . . . heat-dissipating block, 16 . . . void, 18 . . . sound absorbing material.

The invention claimed is:

1. An ultrasonic probe comprising:
a transducer for transmitting/receiving ultrasonic waves to and from an object to be examined; and
a backside section imposed on the backside of the transducer,
wherein the backside section includes:
a first attenuation section disposed in the backside of the transducer for attenuating ultrasonic waves effused from the transducer; and
a heat-dissipating section imposed on the backside of the first attenuation section for dissipating heat from the first attenuation section,
wherein the backside section comprises the second attenuation section for further attenuating the ultrasonic waves effused from the transducer, and
wherein the second attenuation section is disposed in the heat-dissipating section, and is formed in a position apart from the bonded surface of the heat-dissipating section thereof and the first attenuation section.

2. The ultrasonic probe according to claim 1, wherein:
the second attenuation section is formed in a position apart from the surface on the transducer side of the first attenuation section.

3. The ultrasonic probe according to claim 1, characterized in that the second attenuation section is formed so that the position of the end surface on the transducer side of the second attenuation section falls on a position apart from the bonded surface in vertical direction to the backside of the transducer, by an integral multiplication of the wavelength of the ultrasonic wave.

4. The ultrasonic probe according to claim 2, characterized in that the second attenuation section is formed so that the position of end surface on the transducer side of the second attenuation section falls on the position apart from the surface on the transducer side of the first attenuation section, by an integral multiplication of the wavelength of the ultrasonic wave, in vertical direction to the backside of the transducer.

5. The ultrasonic probe according to claim 1, wherein the second attenuation section is formed in at least a part of the backside section in longitudinal direction of the transducer.

6. The ultrasonic probe according to claim 1, wherein the second attenuation section is formed in at least a part of the backside section in minor direction of the transducer.

7. The ultrasonic probe according to claim 6, wherein the second attenuation section is formed passing through from one surface of the backside section to the other surface.

8. The ultrasonic probe according to claim 1, wherein:
the heat-dissipating section has a bonded section with the first attenuation section and the extended section extended from the bonded section to the backside of the transducer section in vertical direction; and
the second attenuation section is formed in the bonded section and/or the extended section.

9. The ultrasonic probe according to claim 1, wherein the second attenuation section has at least one void.

10. The ultrasonic probe according to claim 9, wherein the void is formed by two surfaces parallel to the backside of the transducer, and a rounded surface for connecting the two surfaces thereof.

11. The ultrasonic probe according to claim 9, characterized in that a plurality of voids are formed, and two or more of the respective voids are formed so that position of the surface on the transducer side will have the same distance from the bonded surface.

12. The ultrasonic probe according to claim 9, characterized in that a cross-sectional shape of at least one void is formed to be approximately circular in shape.

13. The ultrasonic probe according to claim 9, characterized in that a cross-sectional shape of at least one void is formed to be approximately triangular in shape.

14. The ultrasonic probe according to claim 13, wherein two adjacent voids having the approximately triangular in shape are formed being mutually inverted with respect to vertical direction to the backside of the transducer.

15. The ultrasonic probe according to claim 9, characterized in that an sound absorbing material is filled in at least one of the voids.

16. The ultrasonic probe according to claim 15, characterized in that the sound absorbing material includes silicon or epoxide resin.

17. The ultrasonic probe according to claim 1, wherein the second attenuation section is formed in the heat-dissipating section so that at least part of the heat-dissipating section operates as heat transfer channel in vertical direction to the backside of the transducer.

18. The ultrasonic probe according to claim 1, wherein:
the heat-dissipating section has a first heat-dissipating section that is bonded to the first attenuation section, a second heat-dissipating section formed in a position apart farther from the transducer than the first heat-dissipating section, and a connecting section for thermally and mechanically connecting the first heat-dissipating section and the second heat-dissipating section; and
the second attenuation section is formed being sandwiched between the first heat-dissipating section and the second heat-dissipating section.

19. An ultrasonic diagnostic apparatus comprising:
a probe comprising a transducer for transmitting/receiving ultrasonic waves to/from an object to be examined and a backside section disposed on the backside of the transducer;
a transmission/reception unit for providing drive signals to the probe and processing the receiving signals outputted from the probe;
a phasing addition unit for performing phasing addition on the receiving signals outputted from the transmission/reception unit;
an imaging construction unit for reconstructing ultrasound images based on the receiving signals outputted from the phasing addition unit; and
a display unit for displaying the ultrasound image outputted from the image constructing unit, wherein the backside section has a first attenuation section disposed on the backside of the transducer and attenuates the ultrasonic waves effused from the transducer, and a heat-dissipating section is disposed on the backside of the first attenuation section and dissipates heat from the first attenuation section,
characterized in having a second attenuation section for further attenuating the ultrasonic waves effused from the transducer, and
wherein the second attenuation section is disposed in the heat-dissipating section, and is formed in a position apart from the bonded surface of the heat-dissipating section thereof and the first attenuation section.

20. The ultrasonic probe according to claim 5, wherein the second attenuation section is formed passing through from one surface of the backside section to the other surface.

* * * * *